United States Patent [19]

Nagasawa et al.

[11] Patent Number: 4,650,753

[45] Date of Patent: Mar. 17, 1987

[54] NOVEL SUBSTRATES FOR USE IN MEASURING THE CONCENTRATION OF KALLIKREIN IN URINE

[75] Inventors: Takeshi Nagasawa, Urawa; Yoshio Nakamura; Katsumasa Kuroiwa, both of Koriyama, all of Japan

[73] Assignee: Nitto Boseki Co., Ltd., Fukushima, Japan

[21] Appl. No.: 749,890

[22] Filed: Jun. 27, 1985

[30] Foreign Application Priority Data

Jul. 4, 1984 [JP] Japan .................................. 59-137230

[51] Int. Cl.$^4$ ........................... C12Q 1/38; C07K 5/08
[52] U.S. Cl. ...................................... 435/23; 435/810; 530/331; 530/802
[58] Field of Search .................. 530/331, 802; 435/23, 435/810

[56] References Cited

U.S. PATENT DOCUMENTS

| | | | |
|---|---|---|---|
| 3,884,896 | 5/1975 | Blomback et al. | 530/331 |
| 3,886,136 | 5/1975 | Claeson et al. | 530/331 |
| 4,137,225 | 1/1979 | Afekenstam et al. | 530/331 |
| 4,279,810 | 7/1981 | Claeson et al. | 530/331 |
| 4,327,178 | 4/1982 | Ryan et al. | 530/331 |
| 4,448,715 | 5/1984 | Ryan et al. | 530/331 |
| 4,452,736 | 6/1984 | Nagasawa et al. | 530/331 |
| 4,457,866 | 7/1984 | Karges et al. | 530/331 |

Primary Examiner—Delbert R. Phillips
Attorney, Agent, or Firm—Bert J. Lewen; Henry Sternberg

[57] ABSTRACT

A novel chromogenic and fluorescent substrate for measuring the concentration of kallikrein in urine. The novel substrate according to the present invention has very excellent substrate specificity to kallikreins and good solubility in water or biological test solutions.

The present substrate is therefore useful for measuring the concentration of kallikrein in urine for the diagnosis of hypertension and other diseases caused by the lowering of the concentration of kallikrein.

6 Claims, No Drawings

NOVEL SUBSTRATES FOR USE IN MEASURING THE CONCENTRATION OF KALLIKREIN IN URINE

FIELD OF THE INVENTION

The present invention relates to novel chromogenic and fluorescent substrates for use in measuring the concentration of kallikrein in urine.

Novel substrates for use in measuring the concentration of kallikrein in urine according to the present invention are represented by the general formula (I),

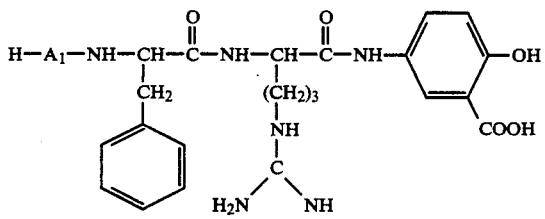

[wherein $A_1$ is Pro (prolyl group), PGlu (pyroglutamyl group), Val (valyl group), Ala (alanyl group), Leu (leucyl group), Phe (phenylalanyl group) or Lys (lysyl group)].

The novel substrates according to the present invention have considerably higher selectivity to kallikrein as compared with any substrate being used in measuring the concentration thereof known in prior art literatures, and thus the substrates according to the present invention can be able to measure the concentration of kallikrein in urine with higher sensitivity.

Kallikrein is enzyme which converts kininogen in plasma into kinin which is pharmacologically active peptide. Biological activities of kallikrein which are performed through the kinin being converted therefrom are activities in increasing for example vasodilation and hypotension or the like.

At the beginning of studies, kallikrein in human urine have been thought as originated in the pancreas. While, recently, they have been thought as originated in the kidney, and thus much attention have been paid to their roles in the renal functions, particularly, it is believed that they are related to control the renal blood flow rate and to adjust the blood pressure. Therefore, decreasing of the biosynthesis and of the secretion of kallikrein will cause serious diseases. For example, the concentration of kallikrein in urine of the patients of essential hypertension and of renal hypertension is considerably lowered as compared with that of a normal healthy person. Additionally, it is known that the concentration of kallikrein in urine of the patients of primary aldosteronism and of Bartter syndrome is higher, while the concentration of kallikrein in urine of the patients of renal failure is lowered.

Therefore measurements of kallikrein in urines of the patients of hypertension and of other diseases are quite important and useful for diagnosis of such disease.

DESCRIPTION OF THE PRIOR ART AND THE PROBLEMS INVOLVED

Methods for determining the activities of kallikrein in human urine have been reported in a number of literatures. However, there have been raised a number of problems in such methods due to their complexity in operations, the influences of inhibitory substances exist in urine and other factors involved therein.

According to the developments in chemistry of synthetic substrates made in recent years, some of methods for determining the activities of kallikrein in human urine have been improved in certain extents. For example, a method for determining the hydrolytic activity of kallikrein against synthetic substrates such as TAME (Tos-Arg-Ome), BAFE (Bz-Arg-OEt), TLME (Tos-Lys-OMe) or the like is, one hand simple in the operation as well as higher repeatability, but on the other hand low in the specificity of the substrates and the sensitivity.

Furthermore, as to the substrate for determining the activities in kallikrein in human urine, there have been developed H-D-Val-Leu-Arg-PNA (S-2266: Kabi), by G. Claeson et al., "Haemostasis, Vol. 7, page 62 (1978)". Similarly, there have also been developed fluorescent peptide of H-Pro-Phe-Arg-MCA (methyl cumarinamide) by coupling with AMC (amino-methylcumarin) which will emit the fluorescence when it is liberated therefrom, by T. Morita et al., "J. Biochem. (Tokyo), Vol. 82, page 1495 (1977)".

On the other hand, as to the synthetic substrate for use in determination of the activity of the enzyme, it is important to satisfy the following four points: (1) high sensitivity to the enzyme to be determined, (2) high specificity to the enzyme to be determined, (3) good solubility in water or biological test solutions, and (4) high detectability for the decomposed substrates. Among these four points, high specificity to the enzyme to be determined is the most important.

In the case of determination of the activity of kallikrein in urine by using chromogenic substrate, the result of determination with high accuracy cannot be expected when interactions were occurred between the substrate and proteolytic enzymes such as plasmin, thrombin, urokinase or the like, other than the kallikrein, which may be existed in the urine. In this connection, it should be noted the fact that, the above-mentioned S-2266 which was developed as the best substrate for use in the determination of kallikrein is not considered as a substrate satisfying the specificity as well as the reactivity. Thus, the above-mentioned substrate of S-2266 may have some dangers to give excess determination results caused by α-thrombin and plasmin which are appearing sometimes in abnormal urine to be examined. Additionally, influences of hydrolysis being caused by urokinase secreted in urine should also be considered when the above-mentioned substrate S-2266 is used.

In addition to the above, in conducting a colorimetry by using a substrate which may be produce yellow color of p-nitroaniline separated from the substrate similar to the above-mentioned substrate of S-2266, the test results obtained therefrom cannot be escaped from the influences of the color of urine sample to be examined.

Furthermore, in conducting a fluorescence method, the test result should be corrected by conducting a blank test for substracting the influences caused by fluorescent substances which may be existed in the urine sample to be examine.

In order to improve such drawbacks shown in conventional substrates, the present inventors have made extensive research and development works for finding novel substrates for use in determination of kallikrein in urine, and as the results, the present inventors have find novel substrates which were improved from the above-mentioned drawbacks as well as possess excellent properties satisfying the above-mentioned essential four conditions.

Thus, the present inventors have succeeded in developing novel substrates for use in determination of kallikdrein in urine of which selectivity was considerably improved as compared with that of conventional substrates of which reactivities against enzymes other than the objective kallikrein in urine, such as plasmin, thrombin, urokinase or the like being inhibited by using 3-carboxy-4-hydroxyanilide (hereinafter referred to as "CHA") in place of p-nitroanilide (hereinafter referred to as "PNA") which was used as the chromogenic group in the substrates being developed before.

SUMMARY OF THE INVENTION

An object of the present invention is to provide novel chromogenic and fluorescent substrates for use in measuring the concentration of kallikrein in urine with higher sensitivity.

Another object of the present invention will be apparent from the descriptions below in this specification.

DETAILED EXPLANATION OF THE INVENTION

Novel chromogenic and fluorescent substrates for use in measuring the concentration of kallikrein in urine according to the present invention are represented by the general formula (I) as follows:

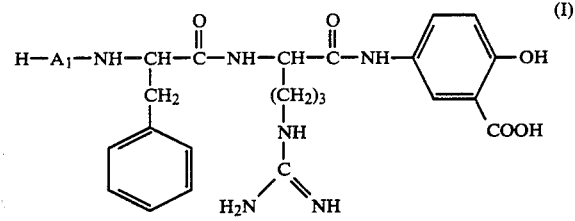

[wherein $A_1$ is Pro (prolyl group), PGlu (pyroglutamyl group), Val (valyl group), Ala (alanyl group), Leu (leucyl group), Phe (phenylalanyl group) or Lys (lysyl group)], specifically the substrate is characterized by the use of 3-carboxy-4-hydroxyaniline (CHA) as the chromogenic group. The present substrate has excellent solubility in water because of the possession of extremely hydrophylic groups, i.e., hydroxyl and carboxyl groups as the chromogenic groups. In a typical examples of practical use as a substrate for the determination of kallikrein in urine, the formed 3-carboxy-4-hydroxyaniline is converted into a colored substance by using a pentacyanoamineferroate method or by an oxydative condensation with a suitable coupler, said colored substance being then subjected to a colorimetric determination. It is also possible to determine the activity of kallikrein in urine specifically by making fluorometric determinations at excitation wavelength of 328 nm and fluorescent wavelength of 540 nm.

The salient features of the present substrate, as stated above, reside in its excellent substrate specificity to kallikrein in urine. As regards to the substrate specificity, the relative reactivity of the present novel substrate PS-2103 (H-D-Ala-Phe-Arg-CHA) in various proteases in urine, that is, kallikrein (HUK), thrombin (TH), plasmin (PL), urokinase (UK) and others is shown in the following Table 1 along with those of PS-2103N (H-D-Ala-Phe-Arg-PNA) and S-2266 which were synthesized as to reference compound by way of using PNA as the chromogenic group with the same amino acid configurations as said novel substrate. In Table 1, the relative reactivity of PS-2103N (H-D-Ala-Phe-Arg-PNA) in each of said enzymes is given as 100 for criterion. As can be seen from Table 1, the relative reactivity to plasmin, thrombin and urokinase is extremely low in the novel substrate using CHA as the chromogenic group. It shows only 4% reactivity to plasmin, 7% reactivity to thrombin and 0% reactivity to urokinase. It is also noted that the novel substrate is markedly improved in its selectivity in comparison with S-2266 which shows 54% reactivity to plasmin, 138% reactivity to thrombin and 217% reactivity to urokinase, specifically, the present novel substrate does not react with urokinase.

The above-mentioned facts indicate that the novel substrate according to the present invention is excellent in determination of kallikrein in urine.

TABLE 1

| Substrate tested | Relative reactivity to enzymes | | | |
|---|---|---|---|---|
| | HUK | TH | PL | UK |
| S-2266 | 225 | 138 | 54 | 217 |
| H—D-Val—Leu—Arg—PNA | (0.245) | (0.065) | (0.067) | (0.013) |
| PS-2103N | 100 | 100 | 100 | 100 |
| H—D-Ala—Phe—Arg—PNA | (0.109) | (0.047) | (0.125) | (0.006) |
| PS-2103 (Substrate of the present invention) H—D-Ala—Phe—Arg—CHA | 242 (0.599) | 7 (0.007) | 4 (0.011) | 0 (0.0) |

Initial substrate concentration $S_0 = 0.4$ m mol. Figures in the parentheses are determined OD (optical density) values.
Determinations were made at wavelength of 405 nm in S-2266 and PS-2103N, and 700 nm in PS-2103.

The primary use of the compound of the present invention is a substrate for determining the activity of kallikrein in urine as already stated. In this case, the substrate is acted to kallikrein in urine in a buffer solution having a pH of 8.5-9.0 and the formed 3-carboxyhydroxyaniline is led into a proper colored substance, and this colored substance is subjected to colorimetric determinations so as to determine the activity of kallikrein in urine. Furthermore, fluorometric determination at an excitation wavelength of 328 nm and a fluorescent wavelength of 540 nm is also possible.

As to the method for leading said reaction product (3-carboxy-4-hydroxyaniline) into a colored substance, a pentacyanoamineferroate method or a method in which said reaction product is subjected to oxidative condensation with a coupler. As to the coupler, an aniline compound, for example, N,N-diethylaniline can be used in case of color development in an acidic condition, and phenol, naphthol, thymol, o-cresol, o-ethylphenol and the like can be used for the color development in an alkaline condition. A variety of oxidizing agents such as hydrogen peroxide, persulfate and the like can be used as the oxidizing agents for oxidative condensation, and particularly metaperiodic acid is perferred.

By the virtue of transformation of 3-carboxy-4-hydroxyaniline into a proper colored substance, the maximum wavelength distribution is confined in the range of 560-770 nm and the variation of coloration due to temperature is minimized and stabilized to provide a situation suited for the determination of the activity of kallikrein in urine. A significant difference in chromogenic sensitivity is also noted. In the case of p-nitroaniline, $\epsilon = 10,600$ at ordinary measuring wavelength of 405 nm, whereas in the pentacyanoamineferroate method, $\epsilon=21,500$ at $\lambda=700$ nm, and in color development by oxidative condensation, in case of o-ethylphenol, $\epsilon=29,000$ at $\lambda=645$ nm, and in case of 2,6-xylenol, $\epsilon=21,600$ at $\lambda=615$ nm. Such high absorbance proves to be greatly helpful for making determinations.

A prominent advantage of the present invention is that the determinations are scarcely affected by the impurities in the urine sample. In the case of p-nitroaniline compounds, determinations are made at a wavelength below 560 nm while according to the present invention, determinations are conducted at a wavelength above 560 nm, so that determinations are kept free of influence by the impurities in the sample, and this, coupled with the intrinsically high specificity of the substrate, makes it possible to obtain a very accurate result of determination.

From the foredoing description, it will be apparent that the compound of the present invention can provide a very excellent substrate to be used for determining the activity of kallikrein as compared with the conventional ones.

The compound of the present invention represented by the general formula (I) can be synthesized by a method well known in peptide chemistry.

As to the α-amino protecting group, it is advantageous to use carbobenzoxy group or t-butyloxycarbonyl group, or the groups related thereto such as p-methoxycarbobenzoxy group, p-nitrocarbobenzoxy group or p-methoxyphenylazolecarbobenzoxy group or the like.

For the protection of γ-guanidyl group of arginine, it is advantageous to use nitro group or protonization means. For the coupling of two amino acids or coupling of α-carboxyl group. For such coupling, N-hydroxysuccinimide, p-nitrophenol, trichlorophenol, 4,6-dimethylpyrimidyl-2-thiol and the like can be used. Abovementioned activation into an ester derivative is advantageously conducted in the presence of a carbodiimide such as N,N-dicyclohexylcarbodiimide (DCC).

For the synthesis of the substrate, a method is used in which chromogenic group is first bonded to arginyl group, followed by successive coupling. Alternatively, N-terminated dipeptide fragment itself may be first synthesized and it is then bonded to arginyl group having chromogenic group.

The present invention will be described in further detail below by way of the embodiments thereof, however it is to be understood that the present invention is not limited only to the scope of these embodiments.

Notice is to be taken of the following matters in reading through the Examples given below.

(1) Abbreviations:
Arg=arginyl
Phe=phenylalanyl
Pro=prolyl
PGlu=pyroglutamyl acid
Val=valyl
Ala=alanyl
Leu=Leucyl
Lys=lysyl
Z=benzyloxycarbonyl
BOC=t-butyloxycarbonyl
DMF=dimethylformamide
MeOH=methanol
NEM=N-ethylmorpholine
—PNA=p-nitroanilide
—CHA=3-carboxy-4-hydroxyanilide
TLC=thin layer chromatography
AcOH=acetic acid
BuOH=butanol
AcOEt=ethyl acetate (Note: The amino acids are defined as all L-isomers unless otherwise noted.)

(2) Thin layer chromatography (TLC):
Silica gel $F_{254}$ plate (manufactured by E. Merck A. G.) was used for TLC analysis.
Solvents used in the TLC are as follows:
$Rf_1$ $CHCl_3$:MeOH:AcOH:$H_2O$=80:40:2.5:5
$Rf_2$ n-BuOH:AcOH:$H_2O$=4:1:1
$Rf_3$ n-BuOH:AcOH:$H_2$=4:1:5

(3) Gel filtration:
"TOYOPEARL HW 40F" a trademark for polyvinyl gel manufactured by Toyo Soda Manufacturing Co., Ltd. was used for the gel filtration.

EXAMPLE 1

Synthesis of H-D-Pro-Phe-Arg-CHA

I. BOC-Arg($NO_2$)-CHA 50.3 Grams (0.158 mole) of BOC-Arg($NO_2$)-OH was dissolved in 160 ml of DMF, to this solution was added 20.5 ml (0.158 mole) of NEM, followed by dropwise addition of 21.2 ml (0.158 mole) of isobutyl chloroformate at $-20°$ C. and reacted for 10 minutes. After the reaction, a solution of 250 ml of DMF, 30.0 g (0.158 mole) of 5-amino-salicylic acid hydrochloride and 61.6 ml (0.474 mole) of NEM was added dropwise to said reaction mixture at $-15°$ to $-10°$ C. After dropwise addition, the reaction was continued at the same temperature for 3 hours, then additionally reacted at room temperature (15° to 20° C.) for 18 hours. After the reaction, DMF was removed by evaporation under reduced pressure and the residue thus obtained was dissolved in 950 ml of AcOEt. The AcOEt solution was washed 4 times with 300 ml of cold 5% hydrochloric acid, washed twice with 300 ml of an aqueous solution saturated with sodium chloride, then decolored and dried with activated carbon and anhydrous magnesium sulfate. After drying, magnesium sulfate and activated carbon were removed by filtration, and the filtrate was cooled and allowed to stand quietly. The crystals precipitated in the filtrate were collected by filtration and dried to obtain 46.2 g (64.3%) of BOC-Arg($NO_2$)-CHA.

$Rf_1$=0.11. Melting point: 208° C. (decomposed).
$[\alpha]_D^{20}$ $-8.4$ (C=1, MeOH).

| Elementary analysis (for $C_{18}H_{26}N_6O_8 \cdot \frac{1}{2}H_2O$) | | | |
|---|---|---|---|
| | C | H | N |
| Calculated (%): | 47.11 | 5.82 | 18.31 |
| Found (%): | 47.16 | 5.75 | 18.30 |

II. BOC-Phe-Arg($NO_2$)-CHA 45.4 Grams (0.1 mole) of BOC-Arg($NO_2$)-CHA was dissolved in 300 ml (0.6 mole) of 2N-HCl/AcOH with a small amount of MeOH, and the mixture was reacted at room temperature for 2 hours. After the reaction was completed, 300 ml of dried diethyl ether was added to the reaction mixture so as to precipitate the crystals. There was obtained 34.9 g (89.4%) of H-Arg($NO_2$)-CHA.HCl.

$Rf_3$=0.31. Melting point: 193°–206° C.
$[\alpha]_D^{20}$+37.4 (C=1, MeOH).

Next, 31.3 g (0.08 mole) of H-Arg($NO_2$)-CHA.HCl was dissolved in 160 ml of 1.5N-NEM/DMF, to this solution was added 31.0 g (0.08 mole) of BOC-Phe-SDP (dimethylmercaptopyrimidine) at 0° to 5° C. and reacted for 18 hours. After the reaction was completed, the reaction mixture was diluted with 1600 ml of AcOEt, and washed twice with 400 ml of cold 5% hydrochloric acid, and washed twice with 400 ml of an aqueous solution saturated with sodium chloride, then there was precipitated crystals. The crystals thus precipitated were collected by filtration and dried to obtain crude BOC-Phe-Arg(NO$_2$)-CHA, then recrystallized from AcOEt/n-hexane to obtain 35.1 g (72.9%) of BOC-Phe-Arg(NO$_2$)-CHA.

Rf$_1$=0.91. Melting point: 212.5° C. (decomposed).
[α]$_D^{20}$ −5.2 (C=1, DMF).

| Elementary analysis (for C$_{27}$H$_{35}$N$_7$O$_9$.H$_2$O) | | | |
|---|---|---|---|
| | C | H | N |
| Calculated (%): | 52.34 | 6.02 | 15.82 |
| Found (%): | 52.43 | 5.79 | 15.64 |

III. BOC-D-Pro-Phe-Arg(NO$_2$)-CHA 34.3 Grams (0.057 mole) of BOC-Phe-Arg(NO$_2$)-CHA was dissolved in 171 ml (0.342 Mole) of 2N HCl/AcOH with a small amount of MeOH, and reacted at room temperature for 2 hours. After the reaction was completed, 2 liters of dried diethyl ether was added to the reaction mixture so as to precipitate crystals. The precipitated crystals were collected by filtration and dried to obtain 30.9 g (100%) of H-Phe-Arg(NO$_2$)-CHA.HCl.

Rf$_2$=0.54. Melting point: 241° C. (decomposed).
[α]$_D^{20}$ −18.0 (C=1.0, DMF).

Next, 1.34 g (2.5 m moles) of H-Phe-Arg(NO$_2$)-CHA was dissolved in 10 ml of 0.75N-NEM/DMF, to this solution was added 0.84 g (2.5 m moles) of BOC-D-Pro-SDP at 0° to 5° C. and reacted at room temperature for 18 hours. After the reaction was completed, the reaction mixture was diluted with 150 ml of AcOEt, and washed 4 times with 50 ml of cold 5% hydrochloric acid, and washed twice with 50 ml of an aqueous solution saturated with sodium chloride, then decolored and dried with activated carbon and anhydrous magnesium sulfate. After drying, magnesium sulfate and activated carbon were removed by filtration, and the solvent was removed from the filtrate by evaporation under reduced pressure to obtain crude product of BOC-D-Pro-Phe-Arg(NO$_2$)-CHA, recrystallized from AcOEt to obtain 1.2 g (85.9%) of BOC-D-Pro-Phe-Arg(NO$_2$)-CHA.

Rf$_1$=0.26. Melting point: 231.5° C. (decomposed).
[α]$_D^{20}$ −2.8 (C=0.5, MeOH).

| Elementary analysis (for C$_{32}$H$_{42}$N$_8$O$_{10}$) | | | |
|---|---|---|---|
| | C | H | N |
| Calculated (%): | 55.01 | 6.06 | 16.04 |
| Found (%): | 54.76 | 6.06 | 15.78 |

IV. H-D-Pro-Phe-Arg-CHA.2HCl 0.90 Gram (1.28 m mole) of BOC-D-Pro-Phe-Arg(NO$_2$)-CHA was dissolved in 3.8 ml of 2N-HCl/AcOH with a small amount of MeOH and reacted at room temperature for 2 hours. After the reaction was completed, the solvent was removed by evaporation under reduced pressure, the residue thus obtained was suspended in 113 ml of MeOH, 37 ml of H$_2$O and 2.2 ml of 1N-HCl. Next, 1 g of palladium black was added thereto and reduced by hydrogenation at 30° C. for 6 hours. After the hydrogenation was completed, the catalyst was removed by filtration and the solvent was also removed by evaporation under reduced pressure. The residue thus obtained was purified by using a gel filtration using TOYOPEARL HW 40F column with MeOH as the developing solvent to obtain 0.66 g (95.3%) of H-D-Pro-Phe-Arg-CHA.2HCl.

Rf$_3$=0.30. Melting point: 230° C.
[α]$_D^{20}$ −5.0 (C=0.5, MeOH).

| Elementary analysis (for C$_{26}$H$_{34}$N$_8$O$_5$.3HCl.H$_2$O) | | | |
|---|---|---|---|
| | C | H | N |
| Calculated (%): | 46.89 | 5.90 | 16.82 |
| Found (%): | 47.01 | 5.62 | 16.88 |

EXAMPLE 2

Synthesis of H-D-Ala-Phe-Arg-CHA

I. Z-D-Ala-Phe-Arg(NO$_2$)-CHA 2.69 Grams (5 m moles) of H-Phe-Arg(NO$_2$)-CHA.HCl was dissolved in 10 ml of 1.5N-NEM/DMF, to this solution was added 1.73 g (5 m moles) of Z-D-Ala-SDP at 0° to 5° C., the reacted at room temperature for 18 hours. After the reaction was completed, the reaction mixture was diluted with 150 ml of AcOEt, the washed 3 times with 50 ml of cold 5%-hydrochloric acid and washed twice with 50 ml of an aqueous solution saturated with sodium chloride, then decolored and dried with activated carbon and anhydrous magnesium sulfate. After the drying, magnesium sulfate and activated carbon were removed by filtration, and the solvent was removed from the filtrate by evaporation under reduced pressure to obtain crude product of Z-D-Ala-Phe-Arg(NO$_2$)-CHA, recrystallized from MeOH/AcOEt/n-hexane to obtain 2.8 g (80.0%) of Z-D-Ala-Phe-Arg(NO$_2$)-CHA.

Rf$_1$=0.91. Melting point: 180°–189° C.
[α]$_D^{20}$ −5.0 (C=1, DMF).

| Elementary analysis (for C$_{33}$H$_{38}$N$_8$O$_{10}$.½H$_2$O) | | | |
|---|---|---|---|
| | C | H | N |
| Calculated (%): | 55.38 | 5.49 | 15.66 |
| Found (%): | 55.08 | 5.69 | 15.36 |

II. H-D-Ala-Phe-Arg-CHA.2HCl 2.3 Grams (3.25 m moles) of Z-D-Ala-Phe-Arg(NO$_2$)-CHA was suspended in a mixed solvent of 113 ml of MeOH, 35 ml of H$_2$O and 2.1 ml of 1N-HCl. To this suspension was added 1 g of palladium black and reduced by hydrogenation at 30° C. for 4 hours. After the hydrogenation was completed the catalyst was removed by filtration, further the solvent was removed by evaporation under reduced pressure. The residue thus obtained was purified by using a gel filtration column of TOYOPEARL HW 40F with MeOH as the developing solvent to obtain 1.5 g (78.2%) of H-D-Ala-Phe-Arg-CHA.2HCl.

Rf$_3$=0.37. Melting point: 185°–210° C.
[α]$_D^{20}$ −12.0 (C=0.5, MeOH).

| Elementary analysis (for C$_{25}$H$_{35}$N$_7$O$_6$Cl$_2$.3H$_2$O) | | | |
|---|---|---|---|
| | C | H | N |
| Calculated (%): | 45.88 | 6.31 | 14.98 |
| Found (%): | 45.41 | 5.88 | 15.33 |

EXAMPLE 3

By a method similar to that described in the previous Examples 1 and 2, there were synthesized substrates as follows:

| Substrate of the present invention | Melting point (°C.) | $Rf_3$ | $[\alpha]_D^{20}$ (C = 0.5 meOH) |
|---|---|---|---|
| PS-2101 H—D-Val—Phe—Arg—CHA | 188–205 | 0.39 | −24.0 |
| PS-2102 H—D-PGlu—Phe—Arg—CHA | 193–206 | 0.29 | −17.0 |
| PS-2104 H—D-Phe—Phe—Arg—CHA | 176–198 | 0.40 | −25.0 |
| PS-2105 H—D-Leu—Phe—Arg—CHA | 185–201 | 0.40 | −24.0 |
| PS-2106 H—D-Lys—Phe—Arg—CHA | 198–213 | 0.14 | −24.0 |

| Elementary analysis | | C | H | N |
|---|---|---|---|---|
| PS-2101 | Calculated (%): | 46.26 | 6.32 | 13.99 |
|  | Found (%): | 46.32 | 6.06 | 14.09 |
| PS-2102 | Calculated (%): | 49.93 | 5.58 | 15.09 |
|  | Found (%): | 50.10 | 5.74 | 14.92 |
| PS-2104 | Calculated (%): | 49.71 | 5.92 | 13.09 |
|  | Found (%): | 49.94 | 5.72 | 13.07 |
| PS-2105 | Calculated (%): | 47.63 | 6.42 | 13.89 |
|  | Found (%): | 47.72 | 6.19 | 14.16 |
| PS-2106 | Calculated (%): | 44.95 | 6.60 | 14.98 |
|  | Found (%): | 45.19 | 6.18 | 14.81 |

EXAMPLE 4

The specificities of newly synthesized substrates were tested by reacting each of them with various enzymes as follows.

(1) Substrate solution: 2 m moles/liter.$H_2O$ (2) Buffer solutions: 50 m moles of tris(hydroxymethyl)aminomethane/hydrochloric acid buffer solution and 150 m moles/liter of NaCl solution were used, and the reaction pH were specified with respect to the enzymes as follows.

| Enzymes | | pH (at 25° C.) |
|---|---|---|
| Human kallikrein in urine | (HUK) | 9.0 |
| Thrombin | (TH) | 8.5 |
| Plasmin | (PL) | 7.8 |
| Urokinase | (UK) | 8.2 |

(3) Enzymes used:

| Enzyme | Origin | Manufacturer | Lot No. | Unit |
|---|---|---|---|---|
| Kallikrein in urine | Human | The Green Cross Corporation | Y1003SM | 0.1 U/ml |
| Thrombin | Bovine | Mochida Pharmaceutical Co., Ltd. | 65146 | 4.0 NIH/ml |
| Plasmin | Human | The Green Cross Corporation | PL-35 | 0.25 CU/ml |
| Urokinase | Human | Mochida Pharmaceutical Co., Ltd. | 2C239 | 1000 U/ml |

(4) Reaction stopper (PNA): 10%-acetic acid (5) Chromogenic reagent (CHA): Pentacyanoamineferroate (6) Method of determination:

0.3 Milliliter of the buffer solution and 0.1 ml of the enzyme reagent were taken in a hard glass test tube of which surface being treated with silicone, or a plastic test tube and preheated in a thermostat at 37° C. for 5 minutes so as to conduct the enzymatic reaction. Precisely 5 minutes after the reaction was started, 2.0 ml of reaction stopper solution or reaction terminating chromogenic reagent was added to terminate the enzymatic reaction. After the enzymatic reaction was completed, the reaction mixture was allowed to stand at 37° C. for 10 minutes, and then the absorbance at 405 nm or 700 nm was measured. The results are shown in the following Table 2.

TABLE 2

| | Comparative test results of substrate specificity | | | | |
|---|---|---|---|---|---|
| | Substrate | HUK | TH | PL | UK |
| 1. S-2266 | H—D-Val—Leu—Arg—PNA | 0.245 | 0.065 | 0.067 | 0.013 |
| 2. PS-2103N | H—D-Ala—Phe—Arg—PNA | 0.109 | 0.047 | 0.125 | 0.006 |
| 3. PS-2100 | H—D-Pro—Phe—Arg—CHA | 0.244 | 0.016 | 0.014 | 0.003 |
| 4. PS-2101 | H—D-Val—Phe—Arg—CHA | 0.501 | 0.025 | 0.025 | 0.0 |
| 5. PS-2102 | H—D-PGlu—Phe—Arg—CHA | 0.128 | 0.005 | 0.016 | 0.0 |
| 6. PS-2103 | H—D-Ala—Phe—Arg—CHA | 0.599 | 0.007 | 0.011 | 0.0 |
| 7. PS-2104 | H—D-Phe—Phe—Arg—CHA | 0.172 | 0.025 | 0.021 | 0.0 |
| 8. PS-2105 | H—D-Leu—Phe—Arg—CHA | 0.144 | 0.054 | 0.044 | 0.0 |
| 9. PS-2106 | H—D-Lys—Phe—Arg—CHA | 0.193 | 0.008 | 0.031 | 0.0 |

The initial substrate concentration $S_0$ = 0.4 m mole.
Figures are the measured values of absorbance (O.D.).
The measurements were conducted at wavelength of 405 nm for the substrate Nos. 1–2, and at wavelength of 700 nm for the substrates Nos. 3–9.

What is claimed is:

1. A composition of matter having the general formula (I):

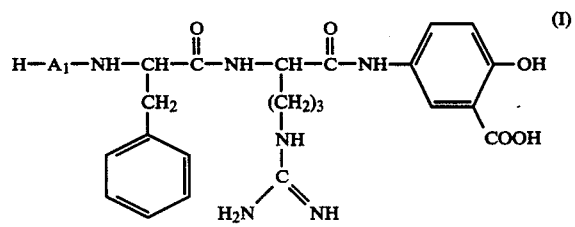

wherein $A_1$ is Pro (prolyl group), PGlu (pyroglutamyl group), Val (valyl group), Ala (alanyl group), Leu (leucyl group), Phe (phenylalanyl group) or Lys (lysyl group) or salt thereof.

2. The composition of matter of claim 1 wherein $A_1$ is a valyl group.

3. The composition of matter of claim 1 wherein $A_1$ is an alanyl group.

4. A method of determining the activity of kallikrein in the urine which comprises reacting a compound having the general formula:

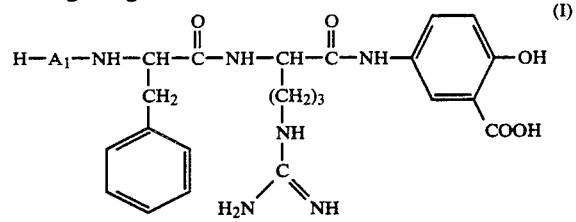

(I)

wherein $A_1$ is Pro (prolyl group), PGlu (pyroglutamyl group), Val (valyl group), Ala (alanyl group), Leu (leucyl group), Phe (phenylalanyl group) or Lys (lysyl group) or salt thereof with urine to form 3-carboxy-4-hydroxy aniline; transforming the 3-carboxy-4-hydroxy aniline into a colored substance; and determining the activity of the kallikrein by colorimetric or fluorometric analysis of the 3-carboxy-4-hydroxy aniline.

5. The method of claim 4 wherein $A_1$ is a valyl group.

6. The method of claim 4 wherein $A_1$ is an alanyl group.

* * * * *